United States Patent [19]
Salo

[11] Patent Number: 5,489,264
[45] Date of Patent: Feb. 6, 1996

[54] PLEURAL DRAINAGE PROBE

[76] Inventor: Gaspar E. Salo, Can Mora del Torrent, 08450 Llinars del Valles (Barcelona), Spain

[21] Appl. No.: 206,963

[22] Filed: Mar. 7, 1994

[30] Foreign Application Priority Data

May 5, 1993 [ES] Spain .................................. 9300589

[51] Int. Cl.⁶ .................................................. A61M 1/00
[52] U.S. Cl. ................................ 604/28; 604/96; 604/101
[58] Field of Search ........................... 604/96, 101, 102, 604/280, 283, 284, 264, 28; 606/191–194

[56]        References Cited

U.S. PATENT DOCUMENTS

| 4,180,076 | 12/1979 | Betancourt | 128/348 |
|---|---|---|---|
| 4,676,778 | 6/1987 | Nelson, Jr. | 604/45 |
| 4,958,634 | 9/1990 | Jang | 604/96 X |
| 5,059,178 | 10/1991 | Ya | 604/101 |
| 5,279,546 | 1/1994 | Mische et al. | 604/101 X |

FOREIGN PATENT DOCUMENTS

| 0421031A1 | 10/1989 | European Pat. Off. . |
|---|---|---|
| 0474906A1 | 9/1990 | European Pat. Off. . |
| 2217606 | 4/1989 | United Kingdom . |

Primary Examiner—John D. Masko
Attorney, Agent, or Firm—Ostrolenk, Faber, Gerb & Soffen

[57]         ABSTRACT

A pleural drainage probe which consists of a flexible tube into which a guide element may be inserted and which is provided with at least two axially separated inflatable peripheral chambers which are both connected to the outside via independent capillary conduits made in the wall of the tube, each of said conduits, after branching close to the end of the tube, terminating in broadenings which enable the air supply means to be connected, each of the branches being provided with an anti-return valve.

1 Claim, 1 Drawing Sheet

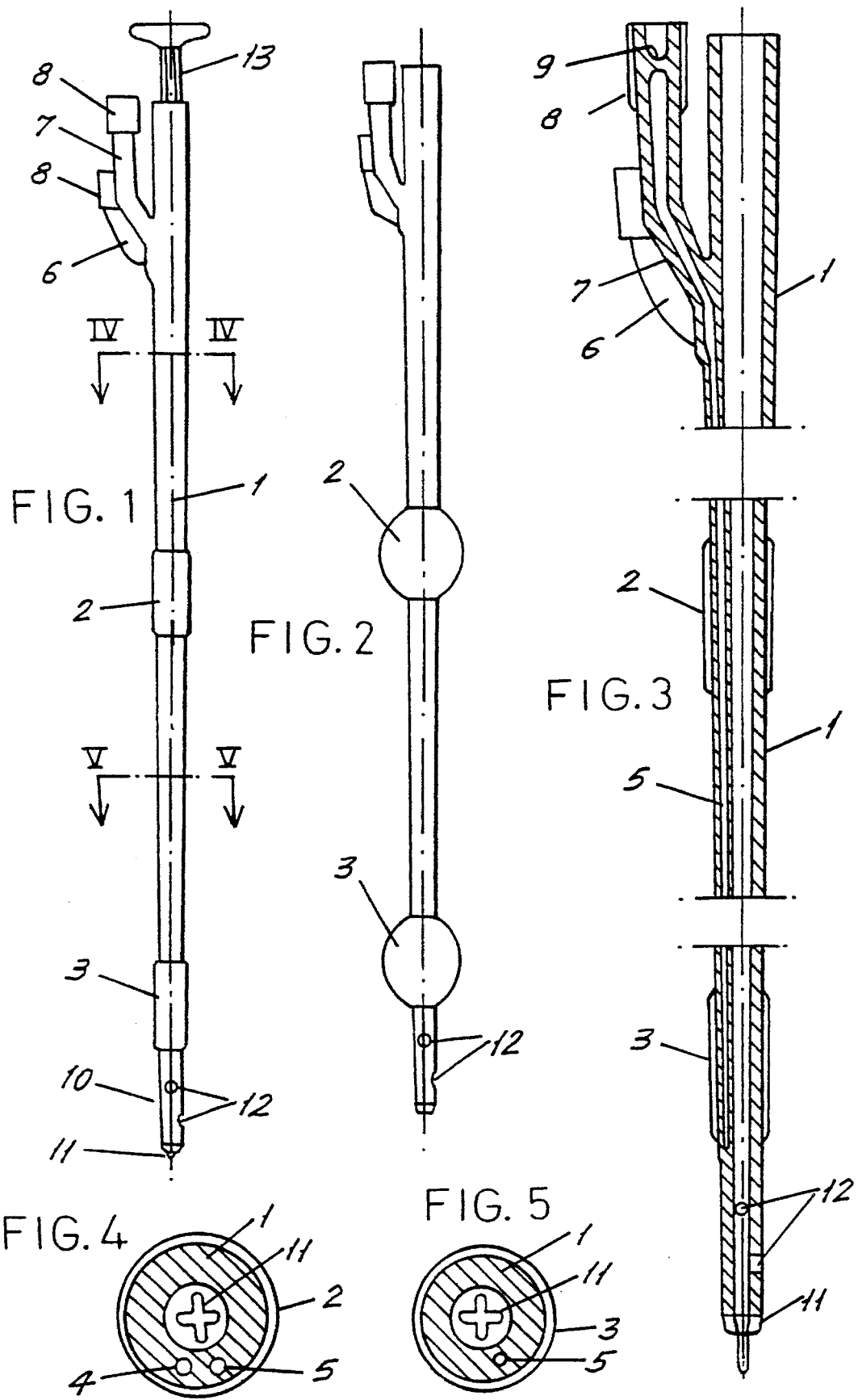

PLEURAL DRAINAGE PROBE

The present invention relates to a pleural drainage probe which includes its own means of fixation to the body of the patient, said means being easy to implant and extract without causing any inconvenience or pain.

More particularly, the probe of the invention is of the type that consists of a flexible tube into which a guide element can be inserted to help the probe to penetrate the body of the patient and which is extracted once the tube has reached the area which is to be drained.

BACKGROUND OF THE INVENTION

Until now the tube used in pleural drainage operations was fixed to the skin of the patient by means of suture stitches, with this fixing system the patient feels the effects during post-operation and it is impractical since the suture stitches can come undone as a result of abrupt movements. Furthermore, when the position of the tube has to be changed the stitches have to be removed so that it can be re-fixed in the right position using the same system, thus causing the patient to suffer unnecessary pain and inconvenience.

SUMMARY OF THE INVENTION

The object of the present invention is a probe of the type described, including its own means of fixation to the body of the patient, said means not causing any inconvenience or pain and making the use of suture stitches unnecessary.

The probe of the invention is characterized in that the flexible tube of which it comprises is provided externally with two inflatable peripheral chambers axially separated from each other along the tube. An independent conduit of capillary section leads from each of those chambers and runs along the wall of the tube towards the end of the probe at which the guide rod is inserted, both tubes opening to the outside close to said end via branches which each incorporate an anti-return valve that enables air to pass in the input and output direction as desired. Furthermore, these branches terminate in broadenings adapted for joining air supply means which may consist, for example, of a syringe.

The other end of the tube which constitutes the probe terminates in a rounded or conical end which is provided with through-holes in its wall.

One of the two peripheral chambers of the probe of the invention is inflated depending on the depth or penetration of the probe into the body of the patient. When a deep point has to be reached, in order to extract air for example, the outermost chamber is inflated, whereas if the depth to be reached is less and the probe does not penetrate as far the innermost chamber is inflated. The relevant chamber is inflated once the probe has been inserted to the required depth. The inflation of the relevant chamber by the expansion of its external wall causes the drainage tube to become fixed inside the body of the patient without producing any unnecessary inconvenience or pain.

The relevant chamber is inflated by means of independent air supply means, for example using two syringes each connected to one of the branches to which the capillary inflation conduits lead.

If necessary, both chambers may be inflated by operating the corresponding air supply means.

BRIEF DESCRIPTION OF THE DRAWINGS

In order that the characteristics and advantages of the present invention be better understood, the accompanying drawings show by way of a non-limiting example one practical embodiment thereof.

In the drawings:

FIG. 1 is a side elevation of a probe according to the invention, arranged to be inserted into the body, FIG. 2 is a similar view to that of FIG. 1 showing the peripheral chambers inflated, FIG. 3 is a enlarged cross sectional view of the probe, FIGS. 4 and 5 are each cross sections, shown to a larger scale, taken along the lines IV—IV and V—V respectively.

DESCRIPTION OF A PREFERRED EMBODIMENT

The probe of the present, the probe of the invention includes a flexible tube 1 which is provided with two inflatable peripheral chambers 2 and 3 that are axially separated from each other. As can best be seen in FIG. 3, these chambers are defined by an annular wall in the form of an elastic membrane which can be fixed by welding to the external surface of the tube 1.

Independent conduits 4 and 5, of capillary section, lead from each of the chambers 2 and 3 and run inside and along the wall of said tube. The two conduits open to the outside via rear branches 6 and 7, each of which terminates in a section 8 adapted for connecting air supply means, said section including a an anti-return valve 9 that enables air to pass in the input and output direction as desired. The other end of the tube 1, beyond the inflatable chamber 3, terminates in a section 10 which is provided with through-holes 11 and 12 in its wall.

The air supply means which can be connected to the section 8 of the branches 6 and 7 may consist of syringes by means of which the chambers 2 and 3 can be inflated such they assume the configuration shown in FIG. 2.

FIG. 4 shows both of the inflation conduits 4 and 5 of the chambers 2 and 3, whilst FIG. 5 shows only the inflation conduit 5 of chamber 3.

A rigid guide element 13, which can have a starshaped cross section for example, is inserted into the flexible tube 1 via the rear end thereof in order that said flexible tube 1 can be inserted into a hole made in the skin of the patient. This element 13 is extracted once the tube is positioned in the area which is to be drained.

If the area to be drained is near the surface, the tube 1 is inserted a relatively short distance and the chamber 3 is inflated such that it acts as a probe retaining and fixing element. If the area or point to be drained is deeper, and the tube 1 has to be inserted further, chamber 2 is inflated. The chambers are inflated by means of different syringes. It may be necessary to inflate both chambers in certain cases.

The probe is preferably made of a contrasting material so that it can be observed using X-rays. The wall or membrane of the chambers 2 and 3 has greater contrast so that it can be distinguished from the rest of the probe.

To extract the probe the inflated chamber or chambers are deflated by inserting a needle or the like into the anti-return valve 9.

I claim:

1. A method for operating in a medical procedure a pleural drainage probe having a flexible tube with a wall and a terminal end and a probe end, two inflatable chambers axially spaced from each other provided on the external periphery of the wall of said flexible tube, a conduit extending from each of said inflatable chambers along the wall of said flexible tube towards said terminal end to an exit from said flexible tube, said two inflatable chambers being inflated and deflated through said inflation conduits, and at least one of said inflatable chambers being adapted to be inflated to the extent to fix said probe in the body of said patient during a medical procedure, the method comprising the steps of:

inserting said pleural drainage probe into the body of a patient; and inflating at least one of said inflatable chambers to the extent to cause said probe to be fixed inside the body of a patient during a medical procedure.

* * * * *